(12) United States Patent
Wille, Jr.

(10) Patent No.: US 7,037,721 B1
(45) Date of Patent: May 2, 2006

(54) PROTEIN-FREE DEFINED MEDIA FOR THE GROWTH OF NORMAL HUMAN KERATINOCYTES

(75) Inventor: John J. Wille, Jr., Trenton, NJ (US)

(73) Assignee: Hy-Gene Biomedical, Inc., Charlotte, NC (US)

( * ) Notice: Subject to any disclaimer, the term of this patent is extended or adjusted under 35 U.S.C. 154(b) by 1105 days.

(21) Appl. No.: 09/694,393

(22) Filed: Oct. 23, 2000

Related U.S. Application Data

(60) Continuation-in-part of application No. 09/271,777, filed on Mar. 18, 1999, now Pat. No. 6,162,643, which is a continuation of application No. 09/133,386, filed on Aug. 13, 1998, now Pat. No. 5,912,175, which is a continuation of application No. 08/893,195, filed on Jul. 15, 1997, now Pat. No. 5,834,312, which is a continuation-in-part of application No. 08/500,744, filed on Jul. 11, 1995, now Pat. No. 5,686,307, which is a continuation of application No. 08/318,221, filed on Oct. 5, 1994, now abandoned, which is a continuation of application No. 08/184,905, filed on Jan. 21, 1994, now abandoned, which is a continuation of application No. 08/063,247, filed on May 18, 1993, now abandoned, which is a division of application No. 07/471,976, filed on Jan. 29, 1990, now Pat. No. 5,292,655.

(51) Int. Cl.
*C12N 5/00* (2006.01)

(52) U.S. Cl. .................. 435/404; 435/405; 435/383; 435/384; 435/325

(58) Field of Classification Search .................. 435/325, 435/383, 384, 404, 405
See application file for complete search history.

(56) References Cited

U.S. PATENT DOCUMENTS 5,753,506 A * 5/1998 Johe
6,030,789 A * 2/2000 Ward et al.

* cited by examiner

*Primary Examiner*—Leon B. Lankford, Jr.
(74) *Attorney, Agent, or Firm*—Standley & Gilcrest LLP

(57) ABSTRACT

Improvements are made to a novel media that replace the requirement for all protein growth factors by the addition to the medium of physiological concentrations of retinyl acetate. The media are serum-free, companion cell or feeder layer-free and organotypic, matrix free solutions for the cultivation of clonally competent basal keratinocytes. The media and methods are useful in the production of epidermal epithelial tissue that is suitable for skin grafting.

6 Claims, 11 Drawing Sheets

EXPERIMENT 2 - PLATE B - 72 HRS
COMPLETE MEDIA W/ PROTEIN GROWTH FACTORS
LIVE CELLS - PHASE CONTRAST MICROSCOPY - 160X

EXPERIMENT 2 - PLATE C - 72 HRS
STANDARD MEDIA W/ RETINYL ACETATE
NO PROTEIN GROWTH FACTORS
LIVE CELLS - PHASE CONTRAST MICROSCOPY - 160X

**EXPERIMENT 2 - PLATE D - 72 HRS
STANDARD MEDIA W/ NO RETINYL ACETATE &
NO PROTEIN GROWTH FACTORS
LIVE CELLS - PHASE CONTRAST MICROSCOPY - 160X**

**EXPERIMENT 2 - PLATE A - 1 HR
TOTAL CELL PLATING
CELLS FIXED AND STAINED -1.25X ACTUAL SIZE
RELATIVE OPTICAL DENSITY UNITS = *1.0***

**EXPERIMENT 2 - PLATE B - 72 HRS
COMPLETE MEDIA W/ PROTEIN GROWTH FACTORS
CELLS FIXED AND STAINED -1.25X ACTUAL SIZE
RELATIVE OPTICAL DENSITY UNITS TO PLATE A = *33.8***

**EXPERIMENT 2 - PLATE C - 72 HRS
STANDARD MEDIA W/ RETINYL ACETATE
NO PROTEIN GROWTH FACTORS
CELLS FIXED AND STAINED -1.25X ACTUAL SIZE
RELATIVE OPTICAL DENSITY UNITS TO PLATE A = 29.7**

EXPERIMENT 2 - PLATE D - 72 HRS
STANDARD MEDIA W/ NO RETINYL ACETATE &
NO PROTEIN GROWTH FACTORS
CELLS FIXED AND STAINED -1.25X ACTUAL SIZE
RELATIVE OPTICAL DENSITY TO PLATE A = 6.7

**RETINYL ACETATE CULTURE TREATMENT
PRE-DISPASE RELEASE OF SKIN SHEET**
PHASE CONTRAST MICROSCOPE
20X MAGNIFICATION

RETINYL ACETATE
*WITHOUT PROTEIN GROWTH FACTORS*
*RETINYL ACETATE* - SKIN SHEET TREATED W/ FBS +1mm $Ca^{++}$ DISPASE TOTAL RELEASE PHASE CONTRAST MICROSCOPE 20X MAGNIFICATION

TOTAL CELL PLATING
*CONTROL*
**PHASE CONTRAST MICROSCOPE
20X MAGNIFICATION**

WITH PROTEIN GROWTH FACTORS
TREATED W/ FBS + 1mm $Ca^{++}$
CONTROL - SKIN SHEET DISPASE RELEASED
PHASE CONTRAST MICROSCOPE
20X MAGNIFICATION

PROTEIN-FREE DEFINED MEDIA FOR THE GROWTH OF NORMAL HUMAN KERATINOCYTES

RELATED APPLICATIONS

This application is a continuation-in-part of U.S. application Ser. No. 09/271,777, now U.S. Pat. No. 6,162,643, issued Dec. 19, 2000, entitled PROCESS AND MEDIA FOR THE GROWTH OF HUMAN EPITHELIA; which is a continuation of U.S. application Ser. No. 09/133,386, filed Aug. 13, 1998, now U.S. Pat. No. 5,912,175; which is a continuation of U.S. application Ser. No. 08/893,195, filed Jul. 15, 1997, now U.S. Pat. No. 5,834,312 issued Nov. 10, 1998, entitled PROCESS AND MEDIA FOR THE GROWTH OF HUMAN EPITHELIA; which is a continuation-in-part of U.S. application Ser. No. 08/500,744, filed Jul. 11, 1995, now U.S. Pat. No. 5,686,307 issued Nov. 11, 1997, entitled SERUM-FREE MEDIUM FOR USE IN THE FORMATION OF A HISTOLOGICALLY COMPLETE LIVING HUMAN SKIN SUBSTITUTE; which is a continuation of U.S. application Ser. No. 08/318,221, filed Oct. 5, 1994, now abandoned; which is a continuation of U.S. application Ser. No. 08/184,905, filed Jan. 21, 1994, now abandoned; which is a continuation of Ser. No. 08/063,247, filed May 18, 1993, now abandoned; which is a divisional of U.S. application Ser. No. 07/471,976, filed Jan. 29, 1990, now U.S. Pat. No. 5,292,655. U.S. Pat. Nos. 5,292,655, 5,686,307, 5,834,312, 5,912,175, and 6,612,643 are incorporated herein by reference.

TECHNICAL FIELD OF THE INVENTION

The field of the invention is in biology and more specifically in the subspecialty of cell biology. The invention relates to a process and cell culture media for the growth of human epithelia, such as gingival epithelium, ureteral epithelium, and corneal epithelium.

BACKGROUND OF THE INVENTION

The epithelium is the membranous cellular tissue that covers the surface or lines a tube or cavity of an animal body. The epithelium serves to enclose and protect the other parts of the body and may produce secretions and excretions and may be associated with assimilation as seen in the gastrointestinal tract. The epithelium is one of the four primary tissues of the body, which constitutes the epidermis and the lining of respiratory, digestive and genitourinary passages. The cornea, which is the transparent part of the coat of the eyeball that covers the iris and pupil and admits light to the interior, is also a tissue that is made of epithelial cells.

The functions of epithelia are varied and include: (1) protective function, by completely covering the external surface (including the gastrointestinal surface, the surface of the whole pulmonary tree including the alveoli and the eye); (2) secretory function, by secreting fluids and chemical substances necessary for digestion, lubrication, protection, excretion of waste products, reproduction and the regulation of metabolic processes of the body; (3) absorptive function, by absorbing nutritive substances and preserving water and salts of the body; (4) sensory function, by constituting important parts of sense organs, especially of smell and taste; and (5) lubricating function, by lining all of the internal cavities of the body, including the peritoneum, pleura, pericardium and the tuncia vaginalis of the testis.

The growth of human epithelial cells without the use of companion-cells, protein growth factors, feeder layers, serum components or organotypic substrates is the advancement in the state of the art that is this invention. Traditionally, tissue culture of normal epithelial cells has been attempted in a variety of commercially available media designed for the growth of less fastidious types of cells, i.e., malignant cells transformed in vitro from cell lines derived from human or non-human tissues, cell lines developed from human or non-human tumors, or cell lines developed for human or non-human embryonic mesenchymal cell types. In contrast, the culture of normal human epithelial stem cells has presented many difficulties not the least of which is the inexorable tendency for these cells to undergo uncontrolled, irreversible, terminal differentiation with the consequent loss of cell division capacity.

A significant development made by Tsao et al. is the formulation of a nutrient medium supplemented with specified growth factors and hormones allowed for the growth of human epidermal cells. See Tsao, M. C. et al., J Cellular Physiol. 110:219–229 (1982). The Tsao medium has been designated MCDB 152. Further refinements of this medium lead to the development of a medium known as MCDB 153. See Boyce, S. T. and Ham, R. G., J Invest. Dermatol. 81:33–40 (1983). The use of these media permitted a more accurate characterization of the necessary growth factors, hormones and $Ca^{2+}$ requirements for retention of high cloning efficiency which is necessary to maintain proper genetic programming for continued subculture of pluripotent basal epidermal stem cells. See Wille, J. J. et al., J Cellular Physiol. 121:31–44 (1984).

The use of serum in cell culture medium provides a complex mixture of growth factors and differentiation-inducing factors. See Pittelkow, M. R. et al., J Invest, Dermatol. 86:410–417 (1986). Pittelkow et al. reported that serum, known to contain fibroblastic cell growth factors, e.g., platelet-derived growth factor, was an inhibitor of basal epidermal cell growth. Further, the differentiation-inducing factors in serum could be equated with serum's content of β-transforming growth factor, (β-TGF). See Shipley, S. D. et al., Cancer Res. 46:2068–2071 (1986). It has also been reported that normal human keratinocytes actually produce their own growth factors. That is, proliferating basal cells are stimulated to secrete α-transforming growth factor (α-TGF) in the presence of added epidermal growth factor (EGF) and decrease production of α-TGF at high cell densities near confluence. Under the latter condition, the arrested cells secrete an inactive form of β-TGF. See Coffey, R. J. et al., Nature 328:817–820 (1987). These considerations led the inventor to the idea that the natural mechanism of growth stimulation and its regulation in cultured epithelia cells could be accomplished through manipulation of the various media components and that such manipulation would also eliminate the need for an organic substrate or organotypic matrix as well.

Judd et al. discuss a keratinocyte growth medium designated keratinocytes-SFM in an article entitled: "Culture of Human Keratinocytes in Defined Serum Free Medium", Focus, 19, No. 1, Pgs. 1–5. This serum-free media is also disclosed in a Gibco Product brochure. However, the actual composition of the SFM media is not disclosed other than it does not contain the growth promoting additives insulin, epidermal growth factor and fibroblast growth factor.

An article by Wille et al., in J Dental Research, 68:1019 (1989) entitled "Serum Free Cultures of Normal Human Gingival Keratinocytes (HGK)" discusses the successful in vitro culturing of human gingival keratinocytes in MCDB 153 medium, supplemented with 0.1 mM ethanolamine, 0.1 mM phosphoethanolamine, 0.5 mM hydrocortisone, 5 µg per ml epidermal growth factor, 5 µg per ml insulin and 35 µg per ml bovine pituitary extract protein where the presence of these proteins is necessary, but their function is unknown in this heterogeneous tissue extract mixture. Wille et al. in The Journal of Cellular Physiology, 150:52–58 (1992) in an article entitled "Effects of Growth Factors, Hormones, Bacterial Lipopolysaccharides and Lipotechoic Acids on the Clonal Growth of Urethreal Epithelial Cells in Serum Free Culture", discloses the use of F-12 media containing bovine pituitary extract and bovine serum albumin for culturing cells isolated from human ureters, again where such tissue products have necessary but unknown effective components.

Chopra et al. in the Journal of Cellular Physiology, 130:173–181 (1987) entitled: "Propagation of Differentiating Normal Human Tracheobronchial Epithelial in Serum Free Medium" discloses the use of a medium similar to MCDB 151 except that it contains 5.4 µg per ml HEPES, 6.1 µg per ml sodium chloride, 0.3 µg per ml sodium acetate and 1 µg per ml sodium bicarbonate. These changes lowered the final osmolarity of the disclosed medium to 290 mosmols. The concentration of HEPES in the Chopra et al. solution was 28 mM.

U.S. Pat. No. 5,328,844 to Moore discloses a culture medium useful for establishing, growing and maintaining mammalian cells in culture, in particular for the establishment of culture of human, normal and malignant cells. The claimed media contains 4,500 mg per liter of HEPES and 5 mg per liter of insulin. This patent does not relate to nor disclose media useful for growth of normal epithelial cells.

In an article by Boisseau et al. entitled "Production of Epidermal Sheets in a Serum Free Culture Medium: A Further Appraisal of the Role of Extracellular Calcium", Journal of Dermatological Science, 3 (1992), 111–120, the author discloses the serum-free media (MCDB 153) to grow keratinocyte monolayers in clonogenic conditions. The effect of extracellular calcium and temperature on proliferation and differentiation of cultured keratinocytes was investigated.

U.S. Pat. No. 4,673,649 to Boyce et al. discloses a basal medium which was MCDB 152 supplemented with epidermal growth factor, transferin, insulin, hydrocortisone, ethanolamine, phosphoethanolamine and progesterone to obtain a medium for growth of human keratinocytes. The inventor of the present application in U.S. Pat. No. 5,292,655 demonstrates that progesterone inhibits optimal growth.

Wilke et al. in "Biologic Mechanisms for the Regulation of Normal Human Keratinocyte Proliferation and Differentiation", American Journal of Pathology, Vol. 131, No. 1, April, 1988, describe a serum-free medium with low calcium concentrations on the order of 0.1 mM. These studies of Wilke et al. actually used MCDB 153 medium supplemented with insulin, EGF and protein of bovine pituitary extract where any effective components are unknown in the extract.

U.S. Pat. No. 5,232,848 to Wolfe et al. discloses a nutrient medium for both high and low density culture of a wide variety of non-epithelial cell lines and cell types. This patent discloses and claims a zwitterionic buffer such as HEPES at a concentration of $2.5 \times 10^{-2}$ moles.

Boyce et al. in U.S. Pat. No. 4,940,666 discloses and claims a growth medium which is free of transferin, comprising complete MCDB 153, EGF and insulin.

Nissley et al. in "Growth and Differentiation of Cells in a Defined Environment", pgs. 337–344 discloses that cells of embryonic and fetal origin produce IGF-1 and IGF-2 which may be important for the control of embryonic and fetal growth. The authors also suggest that the use of these cells could potentially stimulate the growth of the same or neighboring cells and thereby avoid the inclusion of such growth factors in a culture medium.

Boyce et al. in "Calcium Regulated Differentiation of Normal Human Epidermal Keratinocytes in Chemically Defined Clonal Culture and Serum Free Serial Culture", in The Journal of Investigative Dermatology, 81:33S–40S (1983) discloses MCDB 153 supplemented with a number of growth factors and an optimum level of calcium at 0.3 mM for colony forming efficiency and a high calcium concentration of 1.0 mM for induction of stratification and terminal differentiation.

U.S. Pat. No. 5,326,699 to Torishima et al. discloses a serum-free medium for culturing animal epithelial cells comprising 8–14 µg per ml (53.6 mM –93.8 mM) of methionine, up to 0.1 mM of calcium in the form of calcium chloride and other conventional ingredients such as glucose, growth factors, buffers and the like.

U.S. Pat. No. 5,686,307 and U.S. Pat. No. 5,834,312 to Wille disclose a serum-free medium for culturing animal epithelial cells comprising the amino acid histidine (3.0–33 mg/L), isoleucine (3.0–33 mg/L), methionine (4.5–45 mg/L), tryptophan (4.0–44 mg/L) and tryosine (5.0–55 mg/L), NaCl (90–140 mM) and Hepes (14–22 mM) that is useful for the production of a living human skin and animal epithelia. This medium (HECK 109) requires EGF and IGF-1 as the only two protein growth for serial cultivation of proliferating cultures of normal human keratinocytes.

Varani et al. have reported that all-trans retinoic acid stimulates the growth of adult human keratinocytes cultured in a growth factor-deficient medium. Early passage keratinocytes were incubated for 1 or 2 days in a serum-free keratinocyte growth medium (MCDB 153) supplemented with EGF, insulin and BPE and 1.4 mM $Ca^{2+}$ or in growth factor-deprived keratinocyte basal MCDB 153 medium. The cells were concomitantly treated with all-trans retinoic acid (0.1–2.5 ng/ml). Treatment with all-trans retinoic acid inhibited proliferation of keratinocytes that were rapidly growing in the growth-factor supplemented medium. By contrast, all-trans retinoic acid treatment of keratinocytes in growth-factor deficient medium, in which the cells were growth arrested, stimulated growth. Stimulation was observed in a serum-free medium lacking not only protein growth factors, but hydrocortisone, ethanolamine, and phosphoethanolamine. The rate of keratinocyte proliferation in the retinoid-stimulated cultures was approximately 35% of the maximal proliferation rate observed in growth factor supplemented medium. It should be noted that the optimal concentration of all-trans retinoic acid required to produce these effects was 0.5 ng/ml ($1.6 \times 10^{-6}$M). This is about 100-fold greater than the physiological concentration, and is present in amounts known to be damaging to cell membranes. Lower concentration of all-trans retinoic acid were ineffective.

In addition, Marcelo and Dunman (1997) reported that retinoic acid stimulates essential fatty acid-supplemented human keratinocytes. These results were observed in keratinocyte cultures grown in a serum-free medium (MCDB 153) that was supplemented with the protein growth factors, EGF, insulin, and BPE. Finally, Kamata et al. (1999) has reported the growth of oral keratinocytes in a novel protein-free defined medium call PF86-a (Rikimaru et al., 1990) with 85% serum-free medium, MCDB 153 (U.S. Pat. No. 4,673,649). No explanation or hypothesis was given as to what element(s) of the composition were responsible for the ability of these medium to support keratinocyte growth in the absence of protein growth.

A medium that eliminates the use of growth factors in a defined medium would have many technical and commercial benefits. In order to accomplish this goal, the inventor has replaced EGF and IGF-1 in a novel serum-free medium with retinyl acetate. Studies show that sustained growth of human keratinocytes is readily achieved in this improved serum-free medium. In addition, retinyl acetate stimulates proliferation at physiological concentrations unlike the reported effect of all-trans retinoic acid (Varani et al., 1989) and in HECK 109 serum-free medium supplemented with growth hormones (hydrocortisone, ethanolamine, and phosphoethanolamine).

Pellegrini in "Long Term Restoration of Damaged Corneal Surfaces with Autologous Cultured Corneal Epithelium", Lancet, Vol. 349 (1997) discloses the culturing of corneal cells in Dulbecco, Vogt, Eagle's and Ham's F-12 Media containing fetal bovine serum, insulin, transferin, EGF and cholera toxin. The authors' report that cells isolated from the central cornea (limbus) and bulbar conjunctiva could be grown in vitro and then transplanted to the human host.

U.S. Pat. No. 4,304,866 to Green et al. discloses an in vitro method for the formation of epithelial sheets from cultured keratinocytes. The Green method uses a serum containing medium and a feeder layer of murine (mouse) fibroblast cells to accomplish cell growth and differentiation. This procedure has serious limitations for large scale production of human epithelium as the use of serum inextricably confounds the culture of purely basal cells with the dynamics of serum-induced differentiation. The net result is that sub-cultivation of such cultures yields low (<5%) clonal efficiencies preventing step wise large scale build up of uncommitted pluripotent basal cells as a prelude to their conversion into usable sheets of transplantable, histologically-complete, human epithelium. Moreover, the process of Green et al. does not describe the formation of a histologically complete epidermis. The Green et al. procedure forms an epidermis lacking a stratum corneum which is necessary for maximizing the utility of the tissue.

Prior art methods have achieved a complete epidermis, but only in the presence of a complete skin starter sample and serum-containing media that are combined with an organotypic substratum containing growth factors produced by companion cells as disclosed in U.S. Pat. No. 4,485,096. The use of any organotypic substrate as well as feeder or companion cell types, e.g. fibroblasts, seriously limits the resulting products safety and economic viability. See Nanchahal, J. et al. in Lancet II(8656):191–193, (1989).

In order to remedy these deficiencies, the inventor has dispensed with serum-containing media, eliminated any substratum support, dispensed with the requirement for innumerable skin starter samples, and designed a novel and unobvious medium capable of supporting the growth and development of a complete epithelium. Moreover, the identification of essential process steps leading to a functional epithelium has been discovered and can be monitored with specific monoclonal antibodies. The prior art media which contain undefined serum and/or feeder cell factors and/or organotypic substrates and millimolar concentrations of $Ca^{2+}$, high levels of buffers, inadequate levels of amino acids and incorrect osmolalities were not designed for the unlimited proliferation of undifferentiated basal cells. The prior art media allows cultures to spontaneously undergo maturation and uncontrolled differentiation. In contrast, the serum-free media described in this invention produces a complete epithelium.

SUMMARY OF THE INVENTION

There is disclosed an aqueous solution for isolating epithelial cells from animal tissue, said solution comprising:
  a) glucose at a concentration of about 10 mM;
  b) N-(2-OH-ethyl-)piperazine-N'-(2-ethanesulfonic acid) (HEPES) at a concentration of 16–22 mM;
  c) sodium chloride at a concentration of 90–140 mM;
  d) potassium chloride at a concentration of about 3 mM;
  e) sodium orthophosphate ($Na_2HPO_4.7H_2O$) at a concentration of 1 mM;
  f) phenol red at a concentration of 0.0033 mM;
  g) about 100 units of penicillin per ml of solution;
  h) about 100 units of streptomycin per ml of solution; and
  i) one component selected from the group consisting of:
    (i) trypsin at a concentration of 0.1%–0.2% w/v; and
    (ii) soy bean trypsin inhibitor at a concentration of 0.1–1.0% w/v.

The aqueous solution for the isolation of the basal epithelial cells or cell competency solution (CCS) is actually two solutions. The first solution contains trypsin to digest the cells of interest from other cellular tissue. The second solution contains a soybean trypsin inhibitor to stop the digestion of the tissue.

In a more preferred embodiment of the cell competency solution, the sodium chloride is at a concentration of 100 to 130 mM; the HEPES is at a concentration of 18 to 21 mM; the trypsin is at a concentration of 0.12 to 0.18% w/v in the digestion solution and the soybean trypsin inhibitor is at a concentration of 0.3 to 0.8% w/v in the second CCS.

The present invention also relates to a method for the isolation of basal epithelial cells from animal tissues, said method comprising the steps of:
  a) obtaining animal epithelium;
  b) comminuting said epithelium;
  c) placing said comminuted epithelium in the cell competency solution described above containing trypsin at a temperature and for a time sufficient to allow separation of the basal epithelial cells from the epithelium;
  d) collecting said epithelial cells; and
  e) passaging said basal epithelial cells to the CCS containing soybean trypsin inhibitor.

It should be understood that the method described above uses two (2) CCS solutions: (1) a solution containing trypsin to digest the tissue; and (2) a solution containing a soy bean trypsin inhibitor to terminate the digestion of the tissue.

In its broadest sense, the present invention relates to the use of a serum-free medium for culturing animal epithelial cells comprising:
  a) N-(2-OH-ethyl-)piperazine-N'-(2-ethane-sulfonic acid) at a concentration of 14–22 mM;
  b) sodium chloride at a concentration of 100–120 mM;
  c) histidine at a concentration of 0.1–0.25 mM;
  d) isoleucine at a concentration of 0.05–0.5 mM;
  e) methionine at a concentration of 0.1–0.5 mM;
  f) phenylalanine at a concentration of 0.1–0.5 mM;
  g) tryptophan at a concentration of 0.05–0.5 mM; and
  h) tyrosine at a concentration of 0.1–0.5 mM.

This serum-free medium of the invention is sometimes hereinafter referred to as the BASAL medium.

In addition, there is disclosed a protein-free defined medium for the culturing of normal human keratinocytes comprising:
  a) N-(2-OH-ethyl-)piperazine-N'-(2-ethane-sulfonic acid) at a concentration of 14–22 mM;
  b) sodium chloride at a concentration of 100–120 mM;

c) calcium$^{2+}$ ions at a concentration of 0.7–3.0 mM;
d) histidine at a concentration of 0.1–0.25 mM;
e) isoleucine at a concentration of 0.05–0.5 mM;
f) methionine at a concentration of 0.1–0.5 mM;
g) phenylalanine at a concentration of 0.1–0.5 mM;
h) tryptophan at a concentration of 0.05–0.5 mM;
i) tyrosine at a concentration of 0.1–0.5 mM; and
j) retinyl acetate at a concentration of 0.3 ng/ml –33 ng/ml.

This inventive protein-free defined medium is sometimes hereinafter referred to as HECK-110.

In addition, there is disclosed a serum-free medium for culturing epidermal keratinocytes comprising:
a) N-(2-OH-ethyl-)piperazine-N'-(2-ethane-sulfonic acid) at a concentration of 14–22 mM;
b) sodium chloride at a concentration of 100–120 mM;
c) calcium$^{2+}$ ions at a concentration of 0.7–3.0 mM;
d) histidine at a concentration of 0.1–0.25 mM;
e) isoleucine at a concentration of 0.05–0.5 mM;
f) methionine at a concentration of 0.01–0.5 mM;
g) phenylalanine at a concentration of 0.1–0.5 mM;
h) tryptophan at a concentration of 0.05–0.5 mM;
i) tyrosine at a concentration of 0.1–0.5 mM;
j) β-transforming growth factor at a concentration of 3.0–30 ng/ml; and
k) retinyl acetate at a concentration of 0.3–33 ng/ml.

This inventive serum-free medium is sometimes hereinafter referred to as HECK-110 DM.

There is further disclosed a serum-free medium for culturing epidermal keratinocytes comprising:
a) N-(2-OH-ethyl-)piperazine-N'-(2-ethane-sulfonic acid) at a concentration of 14–22 mM;
b) sodium chloride at a concentration of 100–120 mM;
c) calcium$^{2+}$ ions at a concentration of 0.7–3.0 mM;
d) histidine at a concentration of 0.1–0.25 mM;
e) isoleucine at a concentration of 0.05–0.5 mM;
f) methionine at a concentration of 0.1–0.5 mM;
g) phenylalanine at a concentration of 0.1–0.5 mM;
h) tryptophan at a concentration of 0.05–0.5 mM;
i) tyrosine at a concentration of 0.1–0.5 mM;
j) linoleic acid at a concentration of 1–15 ng/ml; and
k) retinyl acetate at a concentration of 0.3–33 ng/ml.

The above described serum-free medium according to the invention is sometimes hereinafter referred to as HECK-110 CM.

The present invention also relates to a method for the formation of a histologically complete, stratified animal epithelium using the media described herein. More specifically, there is disclosed a method for the formation of a histologically complete, stratified human epithelium comprising the steps of:
a) isolation of basal stem cells from animal epithelium using the CCS that contains trypsin;
b) recovering said basal stem cells using CCS that contains soy bean trypsin inhibitor;
c) culturing said isolated basal stem cells in HECK-110 medium to form a confluent sheet of undifferentiated epithelial tissue;
d) culturing said sheet of undifferentiated epithelial tissue in HECK-110 DM to form a sheet of differentiated and stratified tissue; and
e) culturing said differentiated and stratified tissue in HECK-110 CM to form a cornified epithelium.

In a preferred embodiment, the method of the present invention forms a histologically complete human skin.

The invention further relates to the formation of a differentiated and stratified tissue wherein the method is set forth above with the omission of step e) wherein the cornified epithelium layer is formed. The inventive method wherein cornification is omitted is preferably applied to tissue such as skin, cornea and gingiva.

DETAILED DESCRIPTION OF THE INVENTION

Figure 1:
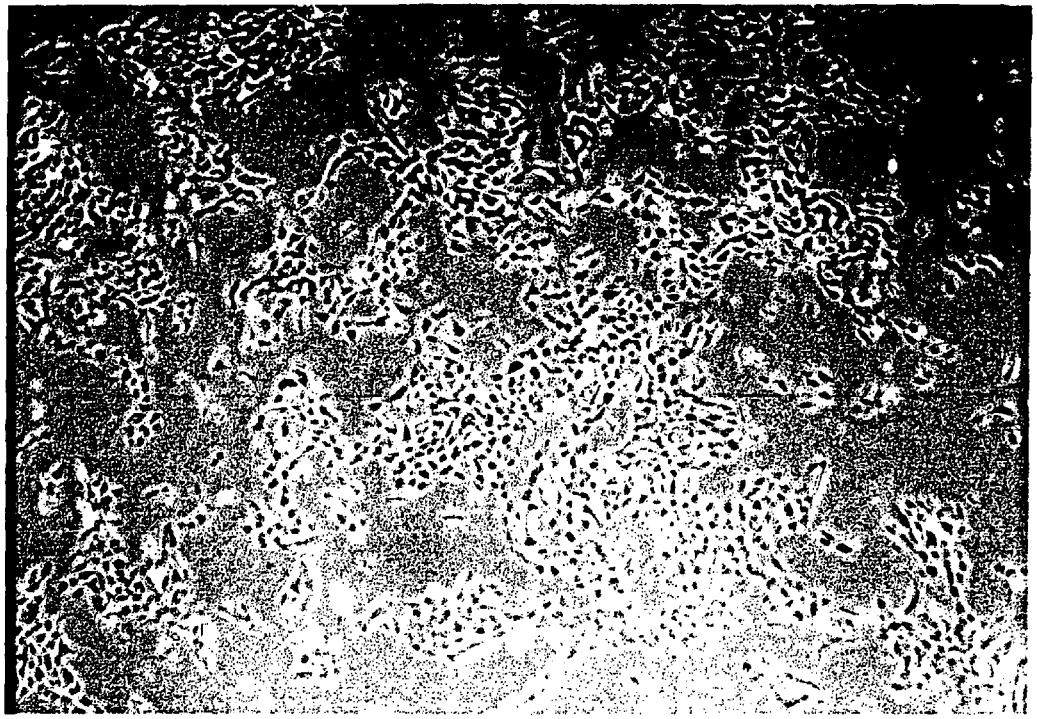
FIGS. 1–3 are phase contrast microscope photomicrographs of living cultures of keratinocytes cultured for 72 hours either in the presence of complete HECK-109 FS medium (B), standard HECK 110 medium (C) or standard HECK 109 medium (D).

The epithelial cells that can be advantageously cultured with the media of this invention include adult epidermal keratinocytes, adult corneal epithelial cells, ureteral epithelial cells, gingival keratinocytes, fetal epithelial cells and the like. As discussed in the Background section, the cell culture media according to the invention are beneficial in growing any epithelium such as the cornea of the eye and linings of the respiratory, digestive and genitourinary tissues.

The present invention also relates to a method of culturing animal epithelia comprising culturing said cells in the serum-free media disclosed above.

The important aspects of the inventive media include the low levels of HEPES, modified levels of amino acids and a particular range of osmolalities. The acceptable osmolarities of the media of this invention can range from 275 to 310 milliosmols per liter of solution (mosmols). Osmolarity is the concentration of an osmotic solution when measured in osmols or milliosmols per liter of solution. The inventor has also found that the reduced levels of HEPES, the sodium chloride concentration, (which is directly related to osmolarity) and the concentration of the six (6) amino acids, allows for the omission of serum and any foreign protein factor in the medium and is the basis for the basal medium hereinafter designated HECK-109. Further, an additional point of novelty resides in the use of retinyl acetate at a concentration of 0.3-33 ng/ml, which eliminates the need for protein growth factors EGF or IGF-1. Additional points of novelty relate to the calcium$^{2+}$ ion concentration of 0.7–3.0 mM and the inclusion of β-transforming growth factor at a concentration of 3.0–30 ng/ml for the differentiation medium hereinafter designated HECK-110 DM. An additional inventive media comprises linoleic acid at a concentration of 1–15 ng per ml for cornification of the reformed tissue hereinafter designated HECK-110 CM.

Admittedly, the prior art is replete with numerous cell culture media. For example, the previously discussed Wolfe, Boyce, Wilke and MCDB media are well known and commercially available. However, none of these references have suggested the removal of all protein growth factors and their replacement with retinyl acetate nor disclosed the improvements the inventor has discovered herein. Those improvements relate to the reduced level of HEPES in combination with the specific and specified levels of six very critical amino acids. Further, while many of the references recite that they are serum-free, they are in fact not tissue-extract free as the various prior art media are taught to utilize various tissue extracts such as bovine pituitary extract.

Most of the major nutrients and other factors essential for cell growth are known and have been used previously and in many permutations. However, the concentrations of certain specific components have been newly formulated for the media of this invention. The components have not merely been optimized but rather a significant discovery has been made in that the components of HEPES and the amino acids are an interrelated set of factors and enhancers for the growth of human epithelial cells. The inventor herein has also discovered that this interrelationship of the various components can also avoid the use of feeder layers such as mouse cells, which are used to produce serum-like growth factors. The novel media of the invention also allows for the avoidance of bovine pituitary extract as taught and suggested by the prior art. As will be demonstrated below, these changes to the media have a profound effect on the media's ability to allow for prolific cell growth and the ultimate differentiation of the cells into a complete epithelium.

An additional aspect of the present invention resides in the discovery that the prior art levels of the aromatic amino acids (histidine, phenylalanine, tryptophan and tyrosine) presented the cultured cells with a rate limiting amount of these vital nutrients. As such, the present inventor has included in his media significantly different amounts of each of these amino acids. Also critically important is the ratio of the amino acids to each other as the ratios impart the ability of this medium to allow the cultured cells to thrive and form a confluent sheet of tissue without the need for serum components or components derived from serum.

The nutrient basal medium designated HECK-109 has as critical components: (i) N-(2-OH-ethyl-)piperazine-N'-(2-ethane sulfonic acid) (hereinafter "HEPES") at 14–22 mM; ii) NaCl at 100–120 mM; and (iii) six (6) key amino acids at about the following concentrations: histidine at $1.0$–$2.5\times10^{-4}$ M; isoleucine at $0.5$–$5.0\times10^{-4}$ M; methionine at $1.0$–$5.0\times10^{-4}$ M; phenylalanine at $1.0$–$5.0\times10^{-4}$ M, tryptophan at $0.5$–$5.0\times10^{-4}$ M; and tyrosine at $10$–$5.0\times10^{-4}$ M. Taken together, HEPES, NaCl and the six (6) key amino acids are superior to any previous media or similar design, in toxicity, osmolarity and support of clonal growth of basal epithelial cells. All media of this invention, except for the CCS, have an osmolarity of between 275 to 310 mosmols.

The novel protein-free defined medium is a serum-free medium for the growth of undifferentiated basal keratinocyte and is based on HECK 109 basal medium and is herein designated HECK-110. HECK- 110 consists of HECK 109 supplemented with retinyl acetate at 0.3–33 ng/ml. This medium is selective for the growth of normal human keratinocytes, and is essential for the formation of a hole-free monolayer (intact sheet) of undifferentiated epidermal cells, while suppressing growth-arrest and commitment to terminal cell differentiation and the loss of clonogenic protential.

The following Examples are intended to be illustrative and not limitative. Values presented in parenthesis are an acceptable range for the given element, unless stated otherwise.

EXAMPLE 1

Primary and Secondary Culture of Normal Human Epidermal Keratinocytes in HECK-110 Protein-Free Defined Medium Isolation of Basal Cells and Primary Cultures Primary cultures of normal human basal epidermal keratinocytes were started by subjecting full-thickness skin samples to enzymatic digestion. Skin obtained from biopsies or autopsies was first cleaned of adhering subdermal fat and the dermis was reduced to less than 3 mm in thickness. The skin sample was then cut into 8 to 12 small pieces (usually 0.5 cm$^2$). These pieces were floated on top of sterile CCS (Cell Competency Solution). CCS consisted of glucose, 10 mM; KCl, 3 mM; NaCl, 130 mM; Na$_2$HPO$_4$.7H$_2$O, 1 mM; phenol red, 3.3 µM; HEPES at 23 mM; (See Shipley, G. D. and Ham, R. G., In Vitro 17:656–670 (1981)) and 0.17% trypsin (w/v) and 100 units/ml of both penicillin and streptomycin. After 14 to 16 hours of digestion at 4° C., the dermis was separated from the epidermis by a split-dermis technique. This was accomplished by placing the cornified side of the epidermis on a clean sterile polystyrene surface whereupon the epidermis spontaneously detaches, and the dermis is removed with sterile forceps. Trypsin digestion cleaves the skin along a fracture line which separates some of the basal cells with the dermis, but frees other basal cells lying between the dermis and the fracture line just above the basal cell layer.

The trypsin-treated epidermis, so split from the dermis, was enriched for a subpopulation of loosely-associated, clonally competent basal cells. In a series of experiments, the inventor herein discovered that these loosely-associated basal cells are larger than the basal cells that remain associated with the dermis. Moreover, these larger basal cells are separable by cell sorting procedures using a fluorescence-activated cell sorting device. They also have a greater colony-forming ability than the dermis-associated basal cells, as demonstrated by clonal growth experimentation.

The loosely-associated basal cells were collected in ice-cold (0°–4° C.) CCS containing 0.1–1.0% w/v SOTI solution in place of the trypsin. The cell suspension was then filtered on ice through a 100 micrometer sized Nylon mesh using sterile procedures. Filtration removes the cell aggregates and ensures preparation of a single cell suspension. The cells were pelleted by low speed-centrifugation (800× g (gravity), 5 mins.) at 4° C. The CCS containing SOTI was aspirated off and the remaining cells were resuspended by gentle pipetting in CCS, and washed once with ice-cold HECK-109 (serum-free basal nutrient medium; see Example 2 for detailed preparation of this medium). The centrifugation step was repeated as above, and the resulting cell pellet was resuspended in 1 to 2 ml of HECK-109. Cell counts were obtained by standard cell chamber counting methods. Primary cultures were initiated into HECK-109 FS supplemented with 0.1 (0.05–0.20) mM ethanolamine; 0.1 (0.5–0.20) mM phosphoethanolamine; 0.5 (0.1–1.0) µM hydrocortisone; and 5 µg/ml EGF. Antibiotics which were added at this time can be removed 2 to 3 days later when the proliferating cell cultures are refed fresh HECK-109 FS. The two protein growth factors (EGF and IGF-1) were added aseptically to the medium. All media was sterilized through a commercially available membrane filter (0.2 microns). The initial seeding density for initiating the primary culture is $5 \times 10^3$ basal cells per cm$^2$ tissue culture flask. Two flasks were set up from an initial yield of 1 to $2 \times 10^6$ cells isolated from the 2 cm$^2$ piece of skin. It should be appreciated that the same isolation procedure used for basal keratinocytes from skin can be used to obtain other basal epithelia cells from tissues such as cornea, gingiva, ureter and the like.

Secondary Culture Procedure--Secondary cultures may be initiated from either primary cultures or early passage secondary cultures. Early passage secondary cultures were passaged by enzymatic dissociation of cells. This serial passage technique is not standard. It involves the use of ice-cold 0.02% (0.02–0.20) SOTI (w/v) in CCS as detailed above for initiating primary cultures. Secondary cultures were seeded at an initial cell density of 1000 cells per cm$^2$ and re-fed HECK-110 medium.

The procedure for calculating colony forming efficiency (CFE) of the basal cells recovered from the epidermis and used to initiate a primary culture is based upon setting up duplicate primary cultures at 5000 cells per cm$^2$ as described above, and then to count the number of cells which attach and later form a colony of at least 8 or more cells, three days after seeding the primary culture. By this method, the percent attachment of epidermal cells was 50 to 60 percent of the input cells.

EXAMPLE 2

Preparation of HECK-110 Basal Nutrient Medium

One aspect of the present invention relates to the preparation of a new media suitable for the large scale amplification of both primary and secondary cultures of normal human epithelial cells, such as keratinocytes, and for conversion of proliferating normal human epithelial monolayer cultures to a fully differentiated tissue transplantable to a human being. More particularly, this Example 2 is directed to the materials and procedures for preparation of a basal nutrient medium (Human Epidermal Cell Keratinocyte, HECK-110), and experiments evidencing its superiority in stimulating epithelial cell growth. The media according to this invention are novel and unobvious by design of the osmolarity, toxicity and pH-buffering properties.

Table 1 below details the concentration of components in basal medium, HECK-110. All biochemicals, growth factors and hormones were purchased from Sigma Chemical Company (St. Louis, Mo., U.S.A.), and all inorganic chemicals were from Fisher Scientific (Pittsburgh, Pa., U.S.A.). All trace elements in Stock T were from Aesor (Johnson Matthey, Inc., Seabrook, N.H., U.S.A., Purotronic Grade). EGF was prepared according to the procedure of Savage, R. C. and Cohen, S. (J. Biol. Chem. 247:7609–7611 (1972)), or purchased from Collaborative Research, Inc., Waltham, Mass.

One liter of HECK-110 was prepared in a separate stock solution fashion as described in Table 1 with respect to Stocks 2 through 10. Medium HECK-110 differs from all other media in the part art by its Stock 1 amino acids, its concentration of NaCl (113 mM; Range 90–140) and HEPES (20 mM; Range 14–22). The concentration of the six (6) amino acids is critical and must be within the following ranges: isoleucine at $0.5–5.0 \times 10^{-4}$ M; histidine at $0.5–2.5 \times 10^{-4}$ M; methionine at $1.0–5.0 \times 10^{-4}$ M; phenylalanine at $1.0–5.0 \times 10^{-4}$ M; tryptophan at $0.5–5.0 \times 10^{-4}$ M; tyrosine at $1.0–5.0 \times 10^{-4}$ M.

TABLE 1

Composition of Basal Nutrient Medium HECK-110

| Stock | Component | Concentration in Final Medium mg/l | mol/l* |
|---|---|---|---|
| 1 | Arginine.HCl | 421.4 | $2.00 \times 10^{-3}$ |
|  | Histidine.HCl.H$_2$O | 36.1 | $1.70 \times 10^{-4}$ |
|  | Isoleucine allo-free | 33.0 | $1.50 \times 10^{-4}$ |
|  | Leucine | 132.0 | $1.00 \times 10^{-3}$ |
|  | Lysine.HCl | 36.6 | $2.00 \times 10^{-4}$ |
|  | Methionine | 45.0 | $3.0 \times 10^{-4}$ |
|  | Phenylalanine | 50.0 | $3.0 \times 10^{-4}$ |
|  | Threonine | 23.8 | $2.00 \times 10^{-4}$ |
|  | Tryptophan | 40.8 | $2.00 \times 10^{-4}$ |
|  | Tyrosine | 54.0 | $3.0 \times 10^{-4}$ |
|  | Valine | 70.2 | $6.00 \times 10^{-4}$ |
|  | Choline Chloride | 27.9 | $2.00 \times 10^{-4}$ |
|  | Serine | 126.1 | $1.20 \times 10^{-3}$ |
| 2 | Biotin | 0.0146 | $6.00 \times 10^{-8}$ |
|  | Calcium Pantothenate | 0.285 | $1.00 \times 10^{-6}$ |
|  | Niacinamide | 0.03363 | $3.00 \times 10^{-7}$ |
|  | Pyridoxal.HCl | 0.06171 | $3.00 \times 10^{-7}$ |
|  | Thiamine.HCl | 0.3373 | $1.00 \times 10^{-6}$ |
|  | Potassium Chloride | 111.83 | $1.50 \times 10^{-3}$ |
| 3 | Folic Acid | 0.79 | $1.80 \times 10^{-6}$ |
|  | Na$_2$HPO$_4$.7H$_2$O | 536.2 | $2.00 \times 10^{-3}$ |
| 4a | Calcium chloride.2H$_2$O | 14.7 | $1.00 \times 10^{-4}$ |
| 4b | Magnesium chloride.6H$_2$O | 122.0 | $6.00 \times 10^{-4}$ |
| 4c | Ferrous sulfate.7H$_2$O | 1.39 | $5.00 \times 10^{-6}$ |
| 5 | Phenol red | 1.242 | $3.30 \times 10^{-6}$ |
| 6a | Glutamine | 877.2 | $6.00 \times 10^{-3}$ |
| 6b | Sodium pyruvate | 55.0 | $5.00 \times 10^{-4}$ |
| 6c | Riboflavin | 0.03764 | $1.00 \times 10^{-7}$ |
| 7 | Cysteine.HCl | 42.04 | $2.40 \times 10^{-4}$ |
| 8 | Asparagine | 13.2 | $1.00 \times 10^{-4}$ |
|  | Proline | 34.53 | $3.0 \times 10^{-4}$ |
|  | Putrescine | 0.1611 | $1.00 \times 10^{-6}$ |
|  | Vitamin B$_{12}$ | 0.407 | $3.00 \times 10^{-7}$ |
|  | Retinyl Acetate | 0.003 | $3.00 \times 10^{-8}$ |
| 9 | Alanine | 8.91 | $1.00 \times 10^{-4}$ |
|  | Aspartic Acid | 3.99 | $3.00 \times 10^{-5}$ |
|  | Glutamic Acid | 14.71 | $1.00 \times 10^{-4}$ |
|  | Glycine | 7.51 | $1.00 \times 10^{-4}$ |
| 10 | Adenine | 12.16 | $9.00 \times 10^{-5}$ |
|  | Inositol | 18.02 | $1.00 \times 10^{-4}$ |
|  | Lipoic Acid | 0.2063 | $1.00 \times 10^{-6}$ |
|  | Thymidine | 0.7266 | $2.00 \times 10^{-6}$ |
| Trace Element T | Copper sulfate | 0.0025 | $1.00 \times 10^{-8}$ |
|  | Selenic Acid | 0.00687 | $3.00 \times 10^{-8}$ |
|  | Manganese Sulfate.5H$_2$O | 0.000241 | $1.00 \times 10^{-9}$ |
|  | Sodium Silicate.9H$_2$O | 0.001421 | $1.00 \times 10^{-7}$ |
|  | Ammonium Molybdate.4H$_2$O | 0.00124 | $1.00 \times 10^{-9}$ |
|  | Ammonium Vanadate | 0.00059 | $1.00 \times 10^{-9}$ |
|  | Nickel Chloride.6H$_2$O | 0.00012 | $5.00 \times 10^{-9}$ |
|  | Stannous Chloride | 0.000113 | $5.00 \times 10^{-10}$ |
|  | Zinc Chloride.7H$_2$O | 0.1438 | $5.00 \times 10^{-7}$ |
| Solids S | Glucose | 1081.0 | $6.00 \times 10^{-3}$ |
|  | Sodium Acetate.3H$_2$O | 500.0 | $3.70 \times 10^{-3}$ |
|  | Sodium Bicarbonate | 1176.0 | $1.40 \times 10^{-2}$ |
|  | Sodium Chloride | 6600.0 | $1.13 \times 10^{-2}$ |
|  | HEPES | 4700.0 | $2.00 \times 10^{-2}$ |

*All above components come together to a final volume of 1 liter of distilled and 0.22 μm filtered water.

The concentrations of these six (6) important amino acids have been shown by the inventor to be necessary for sustained basal cell proliferation. By further experimentation, the inventor discovered that superior growth occurs when the osmolarity of the media are between 275 and 310 milliosmoles (mosmols). The osmolarity of the inventive media are critical to proper cell growth.

Through an extensive series of clonal growth experiments in which the osmolarity was held constant at 300 mosmols and the concentration of HEPES varied between 14 to 28 mM, it was also discovered that the inventive media must incorporate HEPES at between 14–22 mM, preferably between 18 and 22 mM with 22 mM being the most preferred. This is also critical to the media of this invention. Table 2 presents results of clonal growth experiments showing that the design of HECK-109 supports a higher growth rate and a higher colony forming efficiency than a standard MCDB 153 commercial medium.

A most significant aspect of the present invention is that the concentration of 14 to 22 mM concentration HEPES in HECK-109 medium results in a 2 to 3 fold higher colony forming efficiency than that previously attainable. The second significant discovery is that an osmolarity of 280–310 mosmols, most preferably 300 mosmols, of the media permits attainment of higher saturation densities at confluence of the monolayer culture. The third significant discovery is that it is necessary to provide the indicated concentrations of 6 key amino acids present in Stock 1 (typically 2 to 5 times higher concentration than that in commercially available in MCDB 153 medium). This allows human epithelial cell cultures to routinely achieve a cell density equal to or greater than 100,000 cells per cm². HECK-109 incorporates these three discoveries in such a way that the media will allow for and fully support the formation of a complete reformed human epithelium.

EXAMPLE 3

Figure 2:
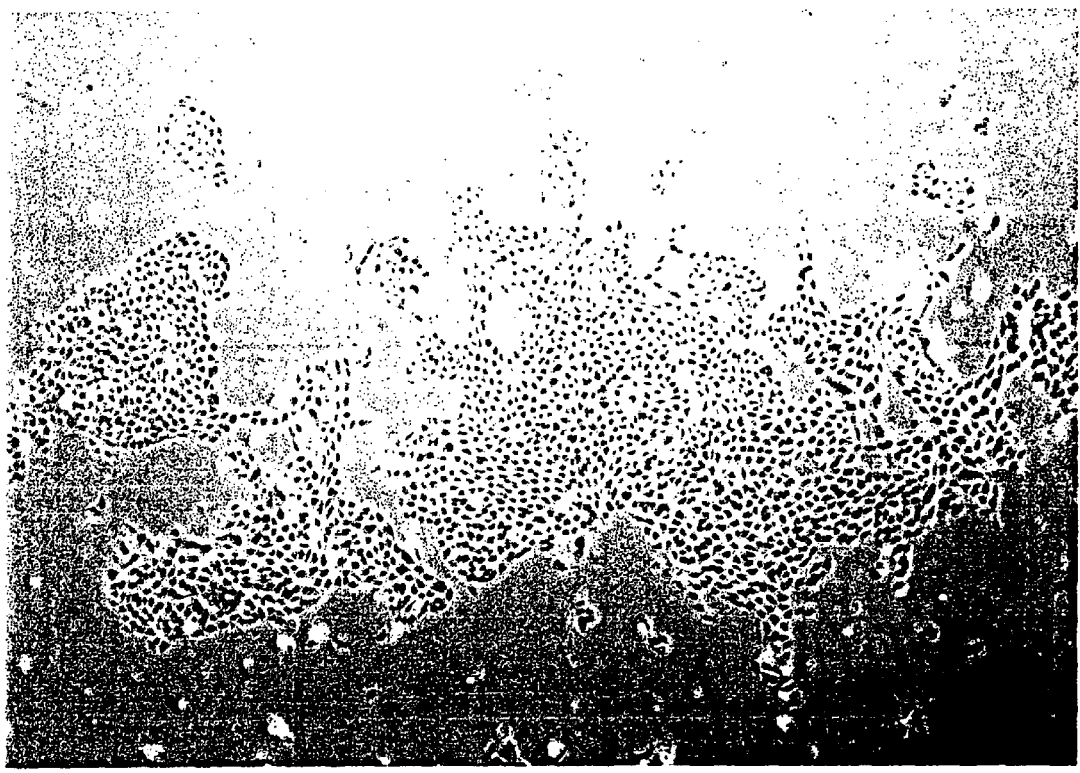
Figure 3:
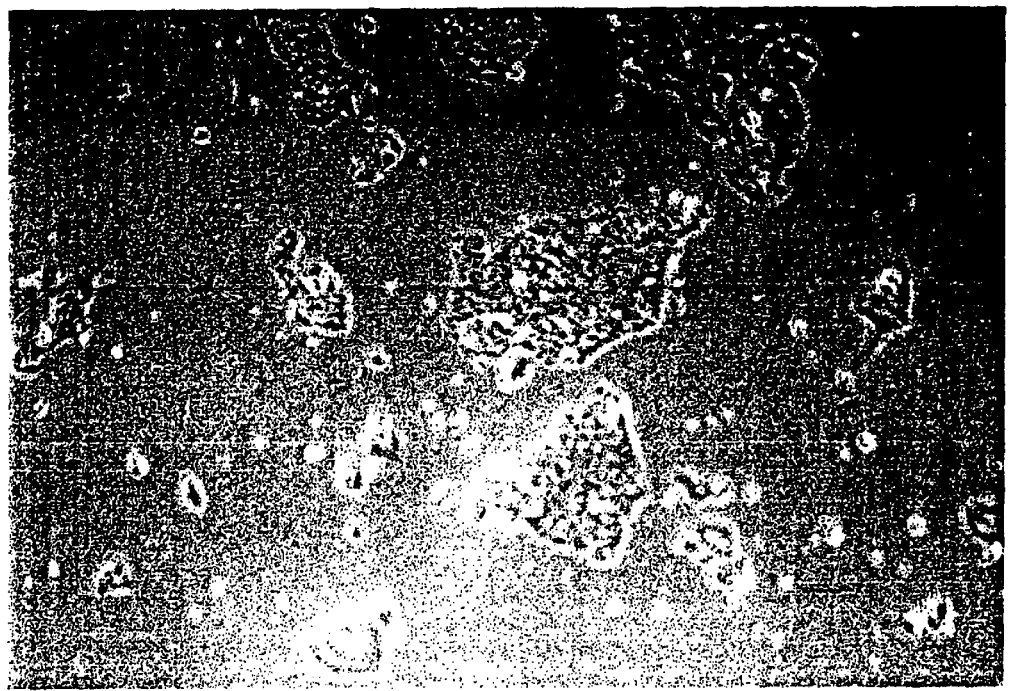

Growth of Secondary Cultures of Normal Human Epidermal Keratincytes in HECK-110 Protein-free Defined Medium Human keratinocyte cultures were initiated from neonatal foreskin as described in Example 1, and then placed in secondary culture in complete HECK-109 FS medium. The purpose of the following experiment was to determine the effect of retinyl acetate on the proliferation of keratinocyte cultures refed HECK-109 basal medium lacking EGF and IGF-1 and supplemented with hydrocortisone, ethanolamine, and phosphoethanolamine. For this purpose, duplicate secondary cultures were refed either 1) complete HECK-109 FS medium (positive control) containing 0.1 mM $Ca^{2+}$, 2) standard HECK-109 medium, i.e., basal medium supplemented with only hydrocortisone, ethanolamine, and phosphoethanolamine, and containing 0.1 mM $Ca^{2+}$ and 3) standard HECK-109 supplemented with retinyl acetate ($3 \times 10^{-8}$M) (now called HECK-110). FIGS. 1–3 are phase contrast microscope photomicrographs of living cultures of keratinocytes cultured for 72 hours either in the presence of complete HECK-109 FS medium (B), standard HECK 110 medium (C) or standard HECK 109 medium (D). Two important observations were made. First, the colony morphology of retinyl acetate treated keratinocyte cultures displays a loose colony configuration, which is characteristic of proliferating cultures and the like that observed for the cultures maintained in growth factor replete medium. In addition, many dividing cells were observed both in the growth factor supplemented and in cultures refed growth factor-deficient medium supplemented with retinyl acetate. None were observed in cultures refed growth factor-deficient medium. The latter displayed a compact colony morphology characteristic of growth-arrested keratinocytes that have committed to terminal cell differentiation. This experiment has been repeated four times with the same results.

Figure 4:
FIG. 4 is a photograph of living cultures of keratinocytes that have been cultured for 1 hour and stained with crystal violet (0.2%).
Figure 5:
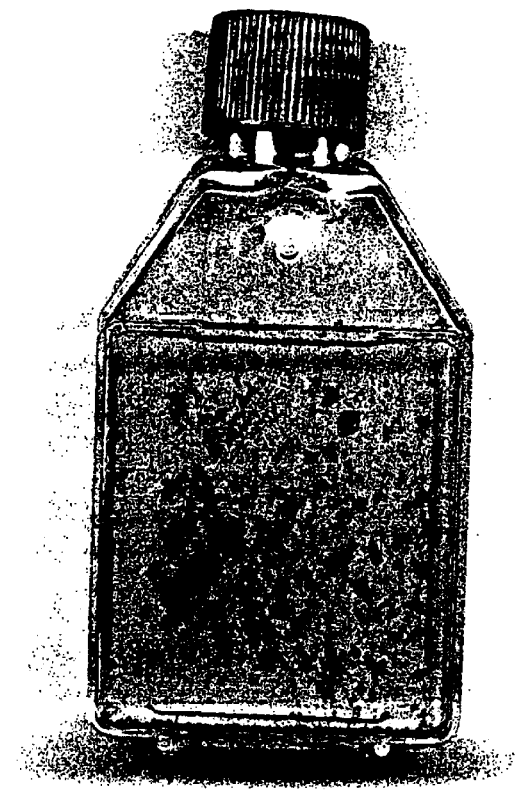
FIGS. 5–7 are photographs of the results of the same experiment in which the cultures were fixed at 72 hours after the above treatments and stained with crystal violet (0.2%).
Figure 6:
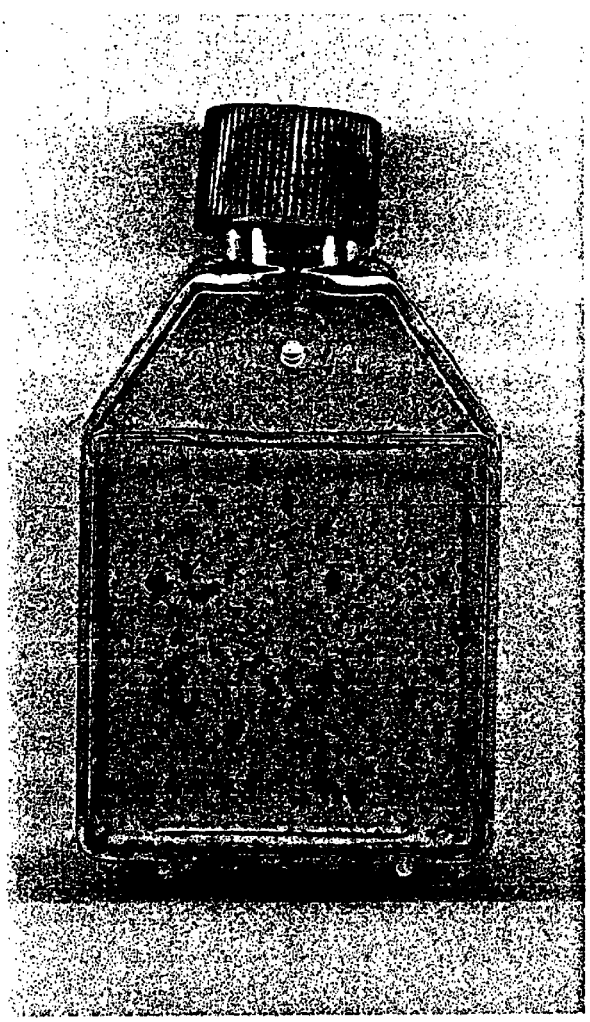
Figure 7:
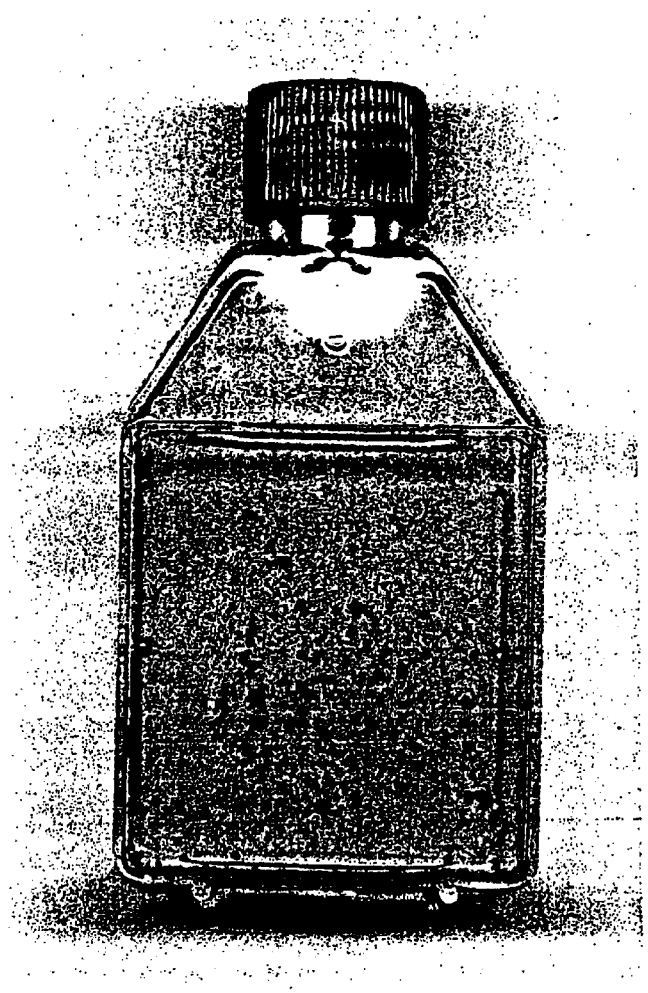

FIG. 4 is a photograph of living cultures of keratinocytes that have been cultured for 1 hour and stained with crystal violet (0.2%). FIGS. 5–7 are photographs of the results of the same experiment in which the cultures were fixed at 72 hours after the above treatments and stained with crystal violet (0.2%). The photographs show that cultures fed complete growth factor containing medium (B) had the most colonies, while cultures refed growth factor-deficient medium supplemented with retinyl acetate (D) has many more colonies than cultures refed only growth-factor deficient standard medium (C).

EXAMPLE 4

Formation of Living Epidermal Sheet Promoted by Protein-Free Medium HECK-110

Figure 8:
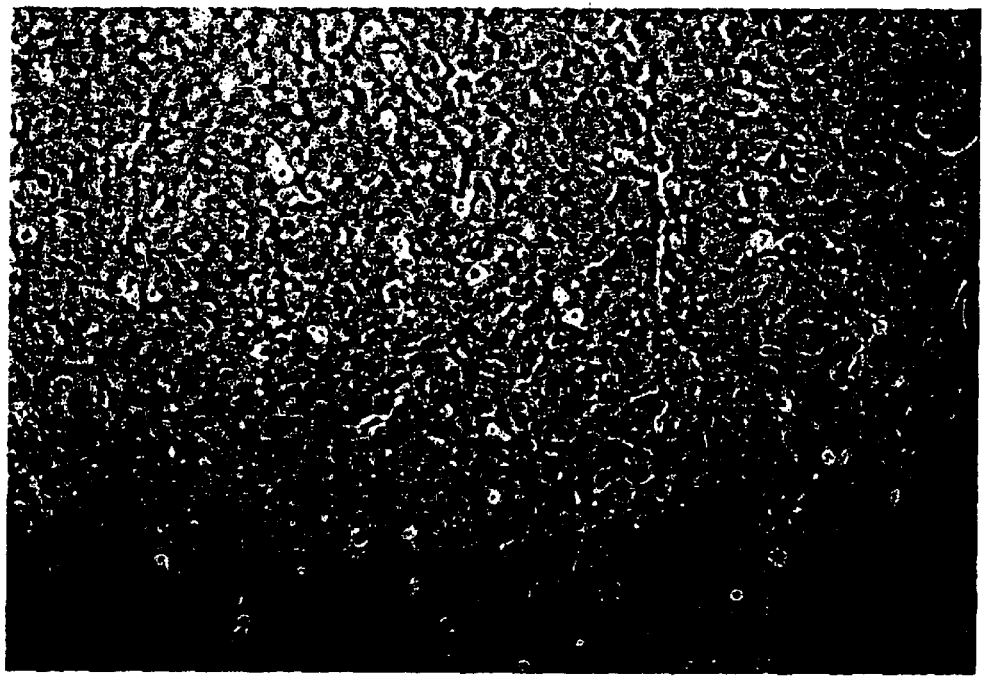
FIG. 8 is a photomicrograph of a phase contrast microscope image of a living epidermal sheet produced by monolayer culture of keratinocytes in the inventive protein-free defined HECK-110 medium, and refed upon reaching confluency with standard HECK medium containing 10% FBS and 1 mM Ca$^{2+}$ ions.
Figure 9:
FIG. 9 is a photomicrograph of a living sheet of epidermis released from the plastic substrate of the culture dish by Dispase proteolytic.
Figure 10:
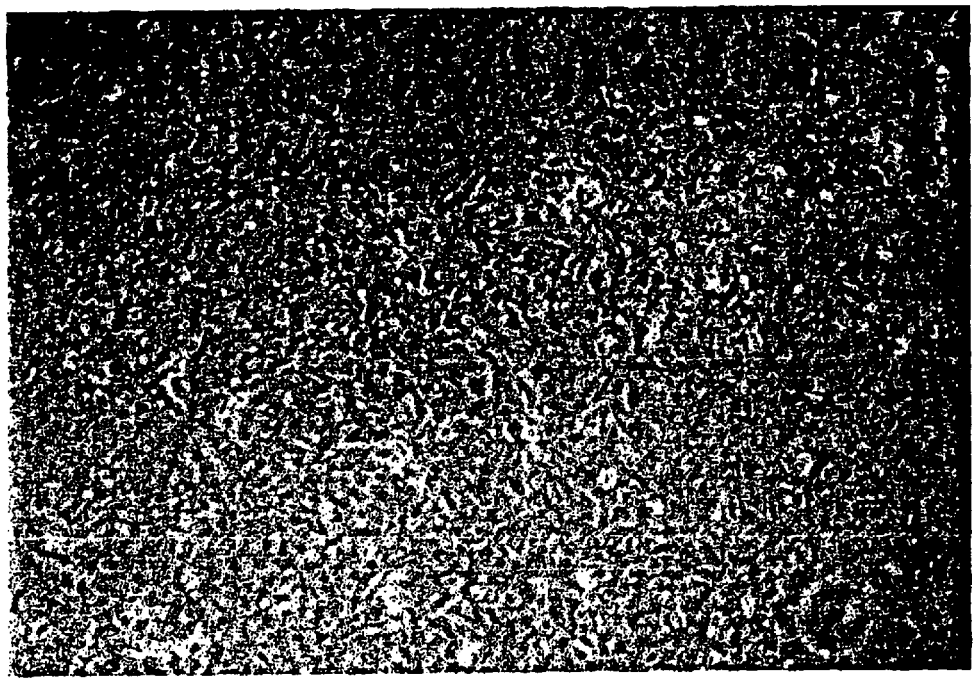
FIGS. 10–11 are photomicrographs of keratinocyte cultures cultured in complete HECK-109 FS medium and treated in an identical manner with 10% FBS and 1 mM Ca$^{2+}$ ions to yield a stratified epidermal epithelium.
Figure 11:

For this example, a viable living epidermal sheet of tissue of normal human keratinocytes was produced by first isolating keratinocytes by use of cell competency solution (CCS, U.S. Pat. No. 5,795,281 to J. Wille), and then culturing the primary culture in complete keratinocyte growth medium (HECK-109 FS), as described in U.S. Pat. No. 5,686,307 to J. Wille. Early passage cultures were further sub-cultivated in (J complete HECK-109 FS. Duplicate low cell density ($5 \times 10^3$/cm²) culture refed protein-free defined HECK-110 medium for an additional 5 days until a confluent monolayer was formed. The cultures were then washed twice with HECK-109 standard media, i.e., basal medium containing ethanolamine ($10^{-4}$ M, and phophoethanolamine ($10^{-4}$ M), and hydrocortisone ($5 \times 10^{-7}$ M), and refed HECK-110 standard medium containing 10% fetal bovine serum and 1 mM $Ca^{2+}$ ions for an additional two days. FIG. 8 is a photomicrograph of a phase contrast microscope image of a living epidermal sheet produced by monolayer culture of keratinocytes in the inventive protein-free defined HECK-110 medium, and refed upon reaching confleuncy with standard HECK medium containing 10% FBS and 1 mM $Ca^{2+}$ ions. FIG. 9 is a photomicrograph of a living sheet of epidermis released from the plastic substrate of the culture dish by Dispase proteolytic enzyme treatment (2 mg/ml for 20 minutes). The general appearance of and morphology of the reformed human epidermis so formed was similar to duplicate keratinocyte cultures cultured in complete HECK-109 FS medium and treated in an identical manner with 10% FBS and 1 mM $Ca^{2+}$ ions to yield a stratified epidermal epithelium (FIGS. 10 and 11).

INDUSTRIAL APPLICABILITY

Significant improvement allows for cell growth without protein or peptide growth factors where retinyl acetate is substituted at physiologically acceptable concentrations. The present invention produces proliferating cultures of keratinocytes that do not require EGF or IGF-1 or any other added protein growth factor. The present invention is directed to the design and formulation of the various novel HECK 110 media, which provide for the differentiation of pluripotent basal epithelial cells to a fully differentiated human epithelium in vitro. HECK-110 is the complete medium for cell growth: HECK-110 DM is for the induction of differentiation and formation of a Malphigian layer and HECK-110 CM is designed for the induction of cellular differentiation in a pre-existing reformed tissue produced by HECK-110 DM. The invention also relates to a method of sequential control for the in vitro construction of a histologically complete living epithelium. The tissue derived from the media and methods of the invention have application for in vitro testing of pharmaceuticals and topical drugs; screening of toxicants, carcinogens, complete or incomplete tumor promoters; evaluation of infective human agents including viruses, e.g., human papilloma viruses, Herpes-simplex viruses and Epstein-Barr virus; and screening of cosmetics.

Most importantly the present invention allows for the use of autologously-derived tissue for transplantation in the treatment of burns or other trauma. Further, the present invention would allow for autologous production of skin, corneal tissue, gingival tissue, ureter tissue and other epithelium for transplant to a patient in need thereof.

Numerous modifications and variations in the invention are expected to occur to those skilled in the art upon considerations of the foregoing descriptions. The invention should not be construed as limited to the preferred embodiments and modes of preparation described herein, since these are to be regarded as illustrative rather than restrictive.

I claim:

1. A protein-free defined medium for culturing epidermal keratinocytes comprising:
    a) N-(2-OH-ethyl-)piperazine-N-(2-ethane-sulfonic acid) at a concentration of 14–22 mM;
    b) sodium chloride at a concentration of 100–120 mM;
    c) histidine at a concentration of 0.1–0.25 mM;
    d) isoleucine at a concentration of 0.05–0.5 mM;
    e) methionine at a concentration of 0.1–0.5 mM;
    f) phenylalanine at a concentration of 0.1–0.5 mM;
    g) tryptophan at a concentration of 0.05–0.5 mM;
    h) tyrosine at a concentration of 0.1–0.5 mM; and
    i) retinyl acetate at a concentration of 0.3–33 ng/ml.

2. A protein-free defined medium for culturing epidermal keratinocytes comprising:
    a) N-(2-OH-ethyl-)piperazine-N'-(2-ethane-sulfonic acid) at a concentration of 14–22 mM;
    b) sodium chloride at a concentration of 100–120 mM;
    c) calcium$^{2+}$ ions at a concentration of 0.7–3.0 mM;
    d) histidine at a concentration of 0.1–0.25 mM;
    e) isoleucine at a concentration of 0.05–0.5 mM;
    f) methionine at a concentration of 0.1–0.5 mM;
    g) phenylalanine at a concentration of 0.1–0.5 mM;
    h) tryptophan at a concentration of 0.05–0.5 mM;
    i) tyrosine at a concentration of 0.1–0.5 mM;
    j) β-transforming growth factor at a concentration of 3.0–30 ng/ml; and
    k) retinyl acetate at a concentration of 0.3–33 ng/ml.

3. A protein-free defined medium for culturing epidermal keratinocytes comprising:
    a) N-(2-OH-ethyl-)piperazine-N'-(2-ethane-sulfonic acid) at a concentration of 14–22 mM;
    b) sodium chloride at a concentration of 100–120 mM;
    c) calcium$^{2+}$ ions at a concentration of 0.7–3.0 mM;
    d) histidine at a concentration of 0.1–0.25 mM;
    e) isoleucine at a concentration of 0.05–0.5 mM;
    f) methionine at a concentration of 0.1–0.5 mM;
    g) phenylalanine at a concentration of 0.1–0.5 mM;
    h) tryptophan at a concentration of 0.05–0.5 mM;
    i) tyrosine at a concentration of 0.1–0.5 mM;
    j) linoleic acid at a concentration of 1–15 ng/ml; and
    k) retinyl acetate at a concentration of 0.3–33 ng/ml.

4. A method for the formation of a histologically complete stratified epidermis comprising the steps of:
    a) isolation of basal stem cells from animal epithelium using a solution comprising:
        i) glucose at a concentration of about 10 mM;
        ii) N-(2-OH-ethyl-)piperazine-N'-(2-ethanesulfonic acid) at a concentration of 16–22 mM;
        iii) sodium chloride at a concentration of 90–140 mM;
        iv) potassium chloride at a concentration of about 3 mM;
        v) sodium orthophosphate (Na$_2$HPO$_4$.7H$_2$O) at a concentration of 1 mM;
        vi) phenol red at a concentration of 0.0033 mM;
        vii) about 100 units of penicillin per ml of solution;
        viii) about 100 units of streptomycin per ml of solution; and
        ix) trypsin at a concentration of 0.1%–0.2% w/v;
    b) recovering said isolated basal stem cells using a solution comprising:
        i) glucose at a concentration of about 10 mM;
        ii) N-(2-OH-ethyl-)piperazine-N'-(2-ethanesulfonic acid) at a concentration of 16–22 mM;
        iii) sodium chloride at a concentration of 90–140 mM;
        iv) potassium chloride at a concentration of about 3 mM;
        v) sodium orthophosphate (Na$_2$HPO$_4$.7H$_2$O) at a concentration of 1 mM;
        vi) phenol red at a concentration of 0.0033 mM;
        vii) about 100 units of penicillin per ml of solution;
        viii) about 100 units of streptomycin per ml of solution; and
        ix) soy bean trypsin inhibitor at a concentration of 0.1%–1.0% w/v;
    c) culturing said isolated basal stem cells in a medium to form a confluent sheet of undifferentiated epithelial tissue, said medium comprising:
        i) N-(2-OH-ethyl-)piperazine-N'-(2-ethanesulfonic acid) at a concentration of 14–22 mM;
        ii) sodium chloride at a concentration of 100–120 mM;
        iii) histidine at a concentration of 0.1–0.25 mM;
        iv) isoleucine at a concentration of 0.05–0.5 mM;
        v) methionine at a concentration of 0.1–0.5 mM;
        vi) phenylalanine at a concentration of 0.1–0.5 mM;
        vii) tryptophan at a concentration of 0.05–0.5 mM;
        viii) tyrosine at a concentration of 0.1–0.5 mM; and
        ix) retinyl acetate at a concentration of 0.3–33 ng/ml;
    d) culturing said sheet of undifferentiated epithelial tissue in a differentiation medium to form a sheet of differentiated and stratified tissue, said differentiation medium comprising:
        i) N-(2-OH-ethyl-)piperazine-N'-(2-ethanesulfonic acid) at a concentration of 14–22 mM;
        ii) sodium chloride at a concentration of 100–120 mM;
        iii) calcium$^{2+}$ ions at a concentration of 0.7–3.0 mM;
        iv) histidine at a concentration of 0.1–0.25 mM;
        v) isoleucine at a concentration of 0.1–05 mM;
        vi) methionine at a concentration of 0.1–0.5 mM;
        vii) phenylalanine at a concentration of 0.1–0.5 mM;
        viii) tryptophan at a concentration of 0.05–0.5 mM;
        ix) tyrosine at a concentration of 0.1–0.5 mM;
        x) β-transforming growth factor at a concentration of 3.0–30 ng/ml; and
        xi) retinyl acetate at a concentration of 0.3–33 ng/ml; and
    e) culturing said differentiated and stratified tissue in a cornification medium to form a cornified epithelium, said cornification medium comprising:
        i) N-(2-OH-ethyl-)piperazine-N'-(2-ethanesulfonic acid) at a concentration of 14–22 mM;
        ii) sodium chloride at a concentration of 100–120 mM;
        iii) calcium$^{2+}$ ions at a concentration of 0.7–3.0 mM;

iv) histidine at a concentration of 0.1–0.25 mM;
v) isoleucine at a concentration of 0.05–0.5 mM;
vi) methionine at a concentration of 0.1–0.5 mM;
vii) phenylalanine at a concentration of 0.1–0.5 mM;
viii) tryptophan at a concentration of 0.05–0.5 mM;
ix) tyrosine at a concentration of 0.1–0.5 mM;
x) linoleic acid at a concentration of 1–15 ng/ml;
xi) retinyl acetate at a concentration of 0.3–33 ng/ml.

5. The method according to claim 4 wherein said histologically complete epidermis is human epidermis.

6. The method according to claim 4, further comprising the step of using serum or tissue extract or animal derived factors or other xenobiotics in combination with $Ca^{2+}$ ions (1–2 mM) in order to form a stratified keratinizing epithelium.

* * * * *

UNITED STATES PATENT AND TRADEMARK OFFICE
CERTIFICATE OF CORRECTION

| | |
|---|---|
| PATENT NO. | : 7,037,721, B1 |
| APPLICATION NO. | : 09/694393 |
| DATED | : May 2, 2006 |
| INVENTOR(S) | : John J. Wille, Jr. |

It is certified that error appears in the above-identified patent and that said Letters Patent is hereby corrected as shown below:

In section (56), please add the following U.S. Patent Documents initialed by the Examiner on September 20, 2001 and inadvertently not cited in the patent as follows:

| | | | |
|---|---|---|---|
| 4,009,282 | 02/22/77 | Voorhees | 514/573 |
| 4,016,036 | 04/05/77 | Green, et al. | 195/1.8 |
| 4,088,756 | 05/09/78 | Voorhees | 514/047 |
| 4,201,788 | 05/06/80 | Voorhees, et al. | 514/081 |
| 4,209,315 | 06/10/80 | Voorhees, et al. | 514/047 |
| 4,304,866 | 12/08/81 | Green, et al. | 435/240 |
| 4,485,096 | 11/27/84 | Bell | 424/95 |
| 4,673,649 | 06/16/87 | Boyce, et al. | 435/240 |
| 4,940,666 | 07/10/90 | Boyce, et al. | 435/240.2 |
| 5,232,848 | 08/03/93 | Wolfe, et al. | 435/240.31 |
| 5,292,655 | 03/08/94 | Wille, Jr. | 435/240.2 |
| 5,326,699 | 07/05/94 | Torishima, et al. | 435/240.2 |
| 5,328,844 | 07/12/94 | Moore | 435/240.31 |
| 5,604,346 | 8/86 | Bell, et al. | 435/1 |
| 5,683,307 | 11/11/97 | Wille, Jr. | 435/405 |
| 5,834,312 | 11/10/98 | Wille, Jr. | 435/405 |
| 5,871,909 | 02/16/99 | ANG.strom, et al. | 435/006 |
| 6,063,606 | 05/2000 | Martin, et al. | 435/189 |

In section (56), please add -- OTHER PUBLICATIONS

"Production of Epidermal Sheets in a Serum Free Culture System: A further appraisal of the role of extracellular calcium," *Journal of Dermatological Science,* 3, Boisseau, et al., Elsevier Science Publishers V.V. (1992) 111-120.

"Reagents, Suppliers and Media Formulations," *Catalogue of Cell Lines & Hybridomas,* American Type Culture Collection, 6th Ed. 1988, pp. 342-343.

"Production and auto-induction of transforming growth factor-α in human keratinocytes," Coffey, Jr., et al., *Nature,* Vol. 328, 27 August 1987, pp. 817-820.

UNITED STATES PATENT AND TRADEMARK OFFICE
CERTIFICATE OF CORRECTION

| | |
|---|---|
| PATENT NO. | : 7,037,721, B1 |
| APPLICATION NO. | : 09/694393 |
| DATED | : May 2, 2006 |
| INVENTOR(S) | : John J. Wille, Jr. |

It is certified that error appears in the above-identified patent and that said Letters Patent is hereby corrected as shown below:

In section (56), please add -- OTHER PUBLICATIONS (cont'd)

"Growth and Differentiation of Human Keratinocytes Without a Feeder Layer or Conditioned Medium," Peehl, et al., *In Vitro*, 1616: 516-525; 1980.

"Improved Medium and Culture Conditions for Clonal Growth with Minimal Serum Protein and for Enhanced Serum-Free Survival of Swiss 3T3 Cells," Shipley, et al., *In Vitro*, Vol. 17, No. 8, August 1981: 1981 Tissue Culture Association, Inc., pp. 656-670.

"Buffer Combinations for Mammalian Cell Culture," *Science*, Vol. 174, pp. 500-503.

"Cultured Cells for Treatment of Disease," Green, *Scientific American*, Nov. 1991, pp. 96-102.

"Culture of Human Keratinocytes in Defined Serum-Free Medium," Judd, et al., *Focus*, 19 No. 1 (1997), pp. 2-5.

"Cultured Composite Skin Grafts: Biological Skin Equivalents Permitting Massive Expansion," Nanchahal, et al., *The Lancet*, July 22, 1989, pp. 191-193.

"Growth of Cells in Defined Environments: The Roleof Endogenous Production of Insulin-like Growth Factors," Nissley, et al., *Growth & Differentiation of Cells in a Defined Environment* (1985) pp. 337-344.

"Long-term restoration of damaged corneal surfaces with autologous cultivated corneal epithelium," Pellegrini, et al., *The Lancet*, Vol. 349, April 5, 1997, pp. 990-993.

UNITED STATES PATENT AND TRADEMARK OFFICE
CERTIFICATE OF CORRECTION

PATENT NO. : 7,037,721, B1
APPLICATION NO. : 09/694393
DATED : May 2, 2006
INVENTOR(S) : John J. Wille, Jr.

It is certified that error appears in the above-identified patent and that said Letters Patent is hereby corrected as shown below:

In section (56), please add -- OTHER PUBLICATIONS (cont'd)

"Calcium-Regulated Differentiation of Normal Human Epidermal Keratinocytes in Chemically Defined Clonal Culture and Serum-Free Serial Culture," Boyce, et al., *The Journal of Investigative Dermatology*, Boyce, et al., Vol. 81, No. 1 Supplement (1983), pp. 33s-40s.

"Cultivating a Cure for Blindness," Hodson, *Nature*, Vol. 387, May 1997, p. 449.

"Clonal Growth of Normal Human Epidermal Keratinocytes in a Defined Medium," Tsao, et al., *Journal of Cellular Physiology* 110:219-229 (1982).

"Ability of Normal Human Keratinocytes that Grow in a Culture in Serum-Free Medium to be Derived from Suprabasal Cells," Wilke, et al., *Journal of the National Cancer Institute,* Vol. 80, No. 16, Oct. 1988, pp. 1299-1304.

"Biologic Mechanisms for the Regulation of Normal Human Keratinocyte Proliferation and Differentiation," Wilke, et al., *American Journal of Pathology,* Vol. 131, April 1988, pp. 171-181.

"Effects of Growth Factors, Hormones, Bacterial Lipopolysaccharides, and Lipotechoic Acids on the Clonal Growth of Normal Ureteral Epithelial Cells in Serum-Free Culture, Wille," et al., *Journal of Cellular Physiology,* 150:52-58 (1992).

"Integrated Control of Growht and Differentiation of Normal Human Prokeratinocytes Cultured in Serum-Free Medium: Clonal Analyses, Growth Kinetics, and Cell Cycle Studies," Wille, Jr., et al., *Journal of Cellular Physiology,* 121:31-44 (1984).

UNITED STATES PATENT AND TRADEMARK OFFICE
CERTIFICATE OF CORRECTION

PATENT NO. : 7,037,721, B1
APPLICATION NO. : 09/694393
DATED : May 2, 2006
INVENTOR(S) : John J. Wille, Jr.

It is certified that error appears in the above-identified patent and that said Letters Patent is hereby corrected as shown below:

In section (56), please add -- OTHER PUBLICATIONS (cont'd)

"Propagation of Differentiating Normal Human Tracheobronchial Epithelial Cells in Serum-Free Medium," Chopra, et al., *Journal of Cellular Physiology* 130: 173-181 (1987).

"Reversible Inhibition of Normal Human Prokeratinocyte Proliferation of Type $\beta$ Transforming Growth Factor-Growth Inhibitor in Serum-free Medium," Shipley, et al., *Cancer Research* 46, 2068-2071, April, 1986.

"Serum-Free Cultures of Normal Human Gingival Keratinocytes (HGK),", Wille, et al., *Journal of Dental Research*, 68, 1019, #1216.

"Two Functionally Distinct Classes of Growth Arrest States in Human Prokeratinocytes that Regulate Clonogenic Potential," Pittelkow, et al., *Journal of Investigative Dermatology*, Vol. 4, April, 1986, pp. 410-417.

Moses, et al. "Growth & Differentiation of Cells in Defined Enviroment (1985) pp. 373-378.

Booyens, et al, "Prostaglandins Leukot. Md.," Jul. 1984, 15 (1) pp. 15-33 (Biosis Abstract #84298492).

The Merck Index, 10$^{th}$ edition, 1983, p. 1172.

Boyce & Ham, *J. Invest. Dermatol.* 81:33-40, 1983 Ca-Reg. differentiation of normal human epid. Keratin In chemical & serum defined Med.

UNITED STATES PATENT AND TRADEMARK OFFICE
CERTIFICATE OF CORRECTION

| | |
|---|---|
| PATENT NO. | : 7,037,721, B1 |
| APPLICATION NO. | : 09/694393 |
| DATED | : May 2, 2006 |
| INVENTOR(S) | : John J. Wille, Jr. |

It is certified that error appears in the above-identified patent and that said Letters Patent is hereby corrected as shown below:

In section (56), please add -- OTHER PUBLICATIONS (cont'd)

"All-Trans Retinoic Acid Stimulates Growth of Adult Human Keratinocytes Cultured in Growth Factor-Deficient Medium, Inhibits Production of Thrombosondin in Fibronectin, and Reduces Adhesion," Varani, et al. *The Society for Investigative Dermatology, Inc.*, 0022-202X/89/S03.50 (1989).

Rikimaru, et al. "Growth of malignant and nonmalignant human squamous cells in a protein-free defined medium, *In Vitro Cell Dev. Biol.*, 26(9):849-56, Sept. 1990 (Medline Abstract).

Diaz, et al. "Regulation of vascular endothelial growth factor expression in human keratinocytes by retinoids, *J. Biol. Chem.* 275(1):642-50, Jan. 7, 2000 (Medline Abstract).

Stoll, et al. "Retinoid regulation of heparin-binding EGF-like growth factor gene expression in human keratinocytes and skin," *Exp. Dermatol.* 7(6):3917, Dec. 1998 (Medline Abstract).

Marcello, et al., "Retinoic acid stimulates essential fatty acid-supplemented human keratinocytes in culture," *J. Invest. Dermatol.*, 108(5):758-62 May 1997 (Medline Abstract).

Jetten "Multi-stage program of differentiation in human epidermal keratinocytes: regulation by retinoids," *J. Invest. Dermatol.*, 85(5):44S-46S Nov. 1990 (Medline Abstract).

UNITED STATES PATENT AND TRADEMARK OFFICE
CERTIFICATE OF CORRECTION

PATENT NO. : 7,037,721, B1
APPLICATION NO. : 09/694393
DATED : May 2, 2006
INVENTOR(S) : John J. Wille, Jr.

It is certified that error appears in the above-identified patent and that said Letters Patent is hereby corrected as shown below:

In section (56), please add -- OTHER PUBLICATIONS (cont'd)

Jee, et al., "Growth and characterization of normal human keratinocytes in F12 serum-free medium," *J. Formos Med. Assoc.* 89(7):559-64 July 1990 (Medline Abstract).

Varani, "Preservation of human skin structure and function in organ culture," *Histol. Histopathol.* 13(3):775-83 July 1998 (Medline Abstract).

Siegenthaler, et al. "Retinol and retinal metabolism. Relationship to the state of differentiation of cultured human keratinocytes," *Biochem J.* 268(2):371-8 June 1, 1990 (Medline Abstract).

Lachgar, et al. "Inhibitory effects of retinoids on vascular endothelial growth factor production by cultured human skin keratinocytes," *Dermatology* 199 Suppl. 1:25-7 1999 (Medline Abstract).

Imanishi, et al. "Growth factors: importance in wound healing and maintenance of transparency of the cornea," *Prog. Retin Eye Res.* 19(1):113-29 Jan. 2000 (Medline Abstract).

Johnson, et al. "Persistence of fetal bovine serum proteins in human keratinocytes," *J. Burn Care Rehabil.*, 11(6) 504-9 Nov.-Dec. 1990 (Medline Abstract).

Schwartz "In vitro growth changes of oral human keratinocytes after treatment with carotenoids, retinoid, and/or DMBA," *Nutr. Cancer*, 33(1):58-68 1999 (Medline Abstract).

UNITED STATES PATENT AND TRADEMARK OFFICE
CERTIFICATE OF CORRECTION

PATENT NO. : 7,037,721, B1
APPLICATION NO. : 09/694393
DATED : May 2, 2006
INVENTOR(S) : John J. Wille, Jr.

It is certified that error appears in the above-identified patent and that said Letters Patent is hereby corrected as shown below:

In section (56), please add -- OTHER PUBLICATIONS (cont'd)

Sass, et al. "Metabolism of topical retinaldehyde and retinol by mouse skin in vivo: predominant formation of retinyl esters and indentification of 14-hydroxy-4, 4-retro-retinol," *Exp. Dermatol.* 5(5):267-71, Oct. 1996 (Medline Abstract).

Marikar, et al. "Retinoic acid receptors regulate expression of retinoic acid 4-hydroxylase that specifically inactivates all-trans retinoic acid in human keratinocyte HaCaT cells," *J. Invest. Dermatol.*, 111(3):434-9 Sept. 1998 (Medline Abstract).

Griffiths, et al. "Short-term retinoic acid treatment increases in vivo, but decreases in vitro, epidermal transglutaminase-K enzyme activity and immunoreactivity," *J. Invest. Dermatol.* 99(3):283-8 Sept. 1992 (Medline Abstract).

Duell, et al. "Human skin levels of retinoic acid and cytochrome P-450-derived 4-hydroxyretinoic acid after topical application of retinoic acid in vivo compared to concentrations required to stimulate retinoic acid receptor-mediated transcription in vitro," *J. Clin. Invest.* 90(4): 1269-74 Oct. 1992 (Medline Abstract).

Duell, et al. "Unoccluded retinol penetrates human skin in vivo more effectively than unoccluded retinyl palmitate or retinoic acid," *J. Invest. Dermatol.* 109(3):301-5 Sept. 1997 (Medline Abstract).

Kang, et al. "Liarozole inhibits human epidermal retinoic acid 4-hydroxylase activity and differentially augments human skin responses to retinoic acid and retinol in vivo," *J. Invest. Dermatol.* 107(2):183-7 Aug. 1996 (Medline Abstract).

UNITED STATES PATENT AND TRADEMARK OFFICE
CERTIFICATE OF CORRECTION

PATENT NO.         : 7,037,721, B1
APPLICATION NO. : 09/694393
DATED                  : May 2, 2006
INVENTOR(S)       : John J. Wille, Jr.

It is certified that error appears in the above-identified patent and that said Letters Patent is hereby corrected as shown below:

In section (56), please add -- OTHER PUBLICATIONS (cont'd)

Kurlandsky, et al; "Auto-regulation of retinoic acid biosynthesis through regulation of retinol esterification in human keratinocytes," *J. Biol. Chem.* 271 (26):15346-52 June 28, 1996 (Medline Abstract).

Varani, et al. "A direct comparison of pharmacologic effects of retinoids on skin cells in vitro and in vivo," *Skin Pharmacol.* 4(4):254-61 1991 (Medline Abstract).

Varani, et al. "Retinoic acid stimulation of human dermal fibroblast proliferation is dependent on suboptimal extracellular Ca2+ concentration," *Am. J. Pathol.* 136(6):1275-81 June 1990 (Medline Abstract).

Varani, et al. "All-trans retinoic acid stimulates growth and extracellular matrix production in growth-inhibited cultured human skin fibroblasts," *J. Invest. Dermatol.* 94(5):717-23 May 1990 (Medline Abstract).

Wang, et al. "Ultraviolet irradiation of human skin causes functional vitamin A deficiency, preventable by all-trans retinoic acid pre-treatment," *Nat. Med.* 5(4):418-22 April 1999 (Medline Abstract).

Xiao, et al. "Identification of heparin-binding EGF-like growth factor as a target in intercellular regulation of epidermal basal cell growth by suprabasal retinoic acid receptors," *EMBO J.* 18(6):1539-48 March 15, 1999 (Medline Abstract).

Griffiths, et al. "Mechanisms of action of retinoic acid in skin repair," *Br. J. Dermatol.* 127 Suppl 4:21-4 Sept. 1992 (Medline Abstract).

UNITED STATES PATENT AND TRADEMARK OFFICE
CERTIFICATE OF CORRECTION

PATENT NO. : 7,037,721, B1
APPLICATION NO. : 09/694393
DATED : May 2, 2006
INVENTOR(S) : John J. Wille, Jr.

It is certified that error appears in the above-identified patent and that said Letters Patent is hereby corrected as shown below:

In section (56), please add -- OTHER PUBLICATIONS (cont'd)

Varani, et al. "Induction of proliferation of growth-inhibited keratinocytes and fibroblasts in monolayer culture by sodium lauryl sulfate: comparison with all-trans retinoic acid," *J. Invest. Dermatol.* 97(5):917-21 Nov. 1991 (Medline Abstract).

Fligiel, et al. "Modulaton of growth in normal and malignant melanocytic cells by all-trans retinoic acid," *J, Cutan Pathol.* 19(1):27-33 Feb. 1992 (Medline Abstract).

Varani, et al. "Inhibition of epithelial cell adhesion by retinoic acid. Relationship to reduced extracellular matrix production and alterations in Ca2+ levels," *Am. J. Pathol.* 138(4):887-95 April 1991 (Medline Abstract).

Varani, et al. "Modulation of Ca2+ levels in keratinocytes by all-trans retinoic acid," *Pathobiology* 60(2):93-9 1992 (Medline Abstract).

Varani, et al. "Molecular mechanisms of intrinsic skin aging and retinoid-induced repair and reversal," *J. Invest. Dermatol. Symp. Proc.* 3(1):57-60 Aug. 1998 (Medline Abstract).

Tavakkol, et al. "Expression of growth hormone receptor, insulin-like growth factor 1 (IFG-1) and IFG-1 receptor mRNA and proteins in human skin," *J. Invest. Dermatol.* 99(3):343-9 Sept. 1992 (Medline Abstract).

Fisher, et al. "Molecular mechanisms of retinoid actions in skin," *FASEB J.* 10(9):1002-13 July 1996 (Medline Abstract).

UNITED STATES PATENT AND TRADEMARK OFFICE
CERTIFICATE OF CORRECTION

PATENT NO. : 7,037,721, B1
APPLICATION NO. : 09/694393
DATED : May 2, 2006
INVENTOR(S) : John J. Wille, Jr.

It is certified that error appears in the above-identified patent and that said Letters Patent is hereby corrected as shown below:

In section (56), please add -- OTHER PUBLICATIONS (cont'd)

Sasaki, et al. "Enhancement by 1 alpha,25-dihydrocyvitamin D3 of chemically induced transformation of BALB 3T3 cells without induction of ornithine decarboxylase or activation of protein kinase C1," *Cancer Res.* 46(2):604-10 Feb. 1986 (Medline Abstract).

Kamata, et al. "Growth of normal oral keratinocyates and squamous cell carcinoma cells in a novel protein-free defined medium," *In Vitro Cell Dev. Biol Anim.* 35(10):63-41 Nov.-Dec. 1999 (Medline Abstract).

Goi, et al "DNA damage-associated dysregulation of the cell cycle and apoptosis control in cells with germ-line p53 mutation," *Cancer Res.* 57(10):1895-902 May 15, 1997 (Medline Abstract).

Kurata, et al. "Effect of eicosapentaenoic acid and arachidonic acid on mouse peritoneal exudate cells and its characteristics," *Yakugaku Zassi* 106(11):1040-4 Nov. 1986 (Japanese language—copy not available) (Medline report).

Kamata, et al. "Growth-inhibitory effects of epidermal growth factor and overexpression of its receptors on human squamous cell carcinomas in culture," *Cancer Res.* 46(4 Pt 1):1648-53 April 1986 (Medline Abstract). --

In section 73, please delete "Hy-Gene Biomedical, Inc., Charlotte, NC (US)" and insert -- Hy-Gene Biomedical Corporation, Ventura, CA (US) --.

UNITED STATES PATENT AND TRADEMARK OFFICE
CERTIFICATE OF CORRECTION

| | |
|---|---|
| PATENT NO. | : 7,037,721, B1 |
| APPLICATION NO. | : 09/694393 |
| DATED | : May 2, 2006 |
| INVENTOR(S) | : John J. Wille, Jr. |

It is certified that error appears in the above-identified patent and that said Letters Patent is hereby corrected as shown below:

In section 74, please delete "Standley & Gilcrest LLP" and insert -- Standley Law Group LLP --.

In column 7, line 20, please delete "0.01" and insert-- 0.1 --.

In column 10, line 52, please delete "speed-centrifugation," and insert-- speed centrifugation --.

In column 12, in Table 1, please delete "Pyridoxal.HCI" and insert -- Pyridoxal·HCI --.

In column 12, in Table 1, please delete "Thiamine.HCI" and insert -- Thiamine·HCI --.

In column 12, in Table 1, please delete "Calcium chloride.$2H_2O$" and insert -- Calcium chloride·$2H_2O$ --.

In column 12, in Table 1, please delete "Magnesium chloride.$6H_2O$" and insert -- Magnesium chloride·$6H_2O$ --.

In column 12, in Table 1, please delete "Ferrous sulfate.$7H_2O$" and insert -- Ferrous sulfate·$7H_2O$ --.

In column 12, in Table 1, please delete "Manganese Sulfate.$5H_2O$" and insert -- Manganese Sulfate·$5H_2O$ --.

In column 12, in Table 1, please delete "Sodium Silicate.$9H_2O$" and insert -- Sodium Silicate·$9H_2O$ --.

UNITED STATES PATENT AND TRADEMARK OFFICE
CERTIFICATE OF CORRECTION

PATENT NO.       : 7,037,721 B1
APPLICATION NO.  : 09/694393
DATED            : May 2, 2006
INVENTOR(S)      : John J. Wille, Jr.

It is certified that error appears in the above-identified patent and that said Letters Patent is hereby corrected as shown below:

In column 12, in Table 1, please delete "Ammonium Molybdate.4H$_2$O" and insert -- Ammonium Molybdate·4H$_2$O --.

In column 12, in Table 1, please delete "Nickel Chloride.6H$_2$O" and insert -- Nickel Chloride·6H$_2$O --.

In column 12, in Table 1, please delete "Zinc Chloride.7H$_2$O" and insert -- Zinc Chloride·7H$_2$O --.

In column 12, in Table 1, please delete "Sodium Acetate.3H$_2$O" and insert -- Sodium Acetate·3H$_2$O --.

In column 14, in line 19, please delete "(J".

In column 16, in line 21, please delete "HPO.sub.4.7H.sub.2O)" and insert-- HPO.sub.4.7H.sub.2 O) --.

Signed and Sealed this

Fourteenth Day of November, 2006

JON W. DUDAS
*Director of the United States Patent and Trademark Office*